United States Patent [19]
Masuzawa et al.

[11] Patent Number: 4,764,608
[45] Date of Patent: Aug. 16, 1988

[54] PROCESS FOR THE MANUFACTURE OF SPIRO-LINKED PYRROLIDINE-2,5-DIONE DERIVATIVES

[75] Inventors: Kuniyoshi Masuzawa, Koga; Kyuya Okamura, Ohmiya; Kazunori Kasuga, Urawa; Shizuyoshi Fujimori, Tochigi; Susumu Kinoshita; Hiroshi Matsukubo, both of Okaya, all of Japan

[73] Assignee: Kyorin Pharmaceutical Co., Ltd., Tokyo, Japan

[21] Appl. No.: 72,050

[22] Filed: Jul. 10, 1987

[30] Foreign Application Priority Data

Jul. 11, 1986 [JP] Japan ................... 61-161790

[51] Int. Cl.⁴ ............... C07D 279/10; C07D 273/01; C07D 221/00
[52] U.S. Cl. ........................... 544/6; 544/70; 546/15
[58] Field of Search ................ 544/6, 70; 546/15

[56] References Cited

U.S. PATENT DOCUMENTS 4,443,465 4/1984 Brittain et al. ............... 546/15
4,593,092 6/1986 Irikura et al. ............... 544/6

FOREIGN PATENT DOCUMENTS 1233684 10/1986 Japan ................... 546/15

OTHER PUBLICATIONS

Takagi et al. Chem. Abstracts, vol. 104, 5884s (1986).

Primary Examiner—Alan L. Rotman
Assistant Examiner—J. Richter
Attorney, Agent, or Firm—Oblon, Fisher, Spivak, McClelland & Maier

[57] ABSTRACT

This invention relates to novel processes for the manufacture of spiro-linked pyrrolidine-2,5-diones of formula;

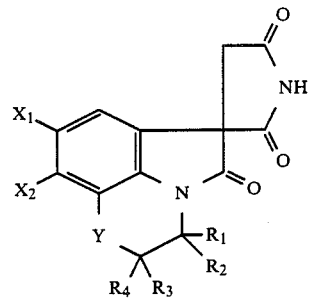

which have a potent inhibitory activity on aldose reductase and are useful for reduction and prevention of chronic diabetic complications.

The invented processes are useful as improved and convenient method for a large scale manufacture.

2 Claims, No Drawings

PROCESS FOR THE MANUFACTURE OF SPIRO-LINKED PYRROLIDINE-2,5-DIONE DERIVATIVES

DETAILED DESCRIPTION OF THE INVENTION

This invention relates to novel processes for the manufacture of spiro-linked pyrrolidine-2,5-diones having a potent inhibitory activity on aldose reductase and which are useful for reduction and prevention of chronic diabetic complications.

In more detail, the invention relates to processes for the preparation of spiro-linked pyrrolidine-2,5-diones represented by the formula;

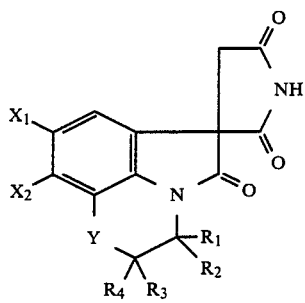

(I)

wherein $X_1$ and $X_2$ each independently represents a hydrogen atom, a halogen atom, a lower alkyl group or a lower alkoxy group; Y is a methylene group, an oxygen atom or a sulfur atom; $R_1$, $R_2$, $R_3$ and $R_4$ each independently represents a hydrogen atom, a lower alkyl group or forming a benzene ring together with their adjacent carbon atoms.

More specifically in the compounds of formula (I), the term "lower alkyl" as used in $X_1$, $X_2$, $R_1$, $R_2$, $R_3$ and $R_4$ means straight or branched hydrocarbons having 1 to 3 carbon atom, such as a methyl, ethyl, n-propyl or isopropyl group. The term "lower alkoxy" as used in $X_1$ and $X_2$ means alkoxy groups having 1 to 3 carbon atoms, such as a methoxy, ethoxy, n-propoxy or isopropoxy group. The term "halogen atom" as used in $X_1$ and $X_2$ means a fluorine, chlorine, bromine or iodine atom. Y means a methylene group, an oxygen atom or a sulfur atom. When $R_1$, $R_2$, $R_3$ and $R_4$ form a ring together with their adjacent carbon atoms, the ring means a benzene ring.

We have already discovered that spiro-linked pyrrolidine-2,5-diones of formula (I) possess potent aldose reductase inhibitory activity and are useful for reduction and prevention of chronic diabetic complications (Japan Kokai JP 60-142984, U.S. Pat. No. 4,593,092).

The process for preparing the compounds of formula (I) described in Japan Kokai JP No. 61-142984 (hereinafter called as the former method is cited in below scheme.

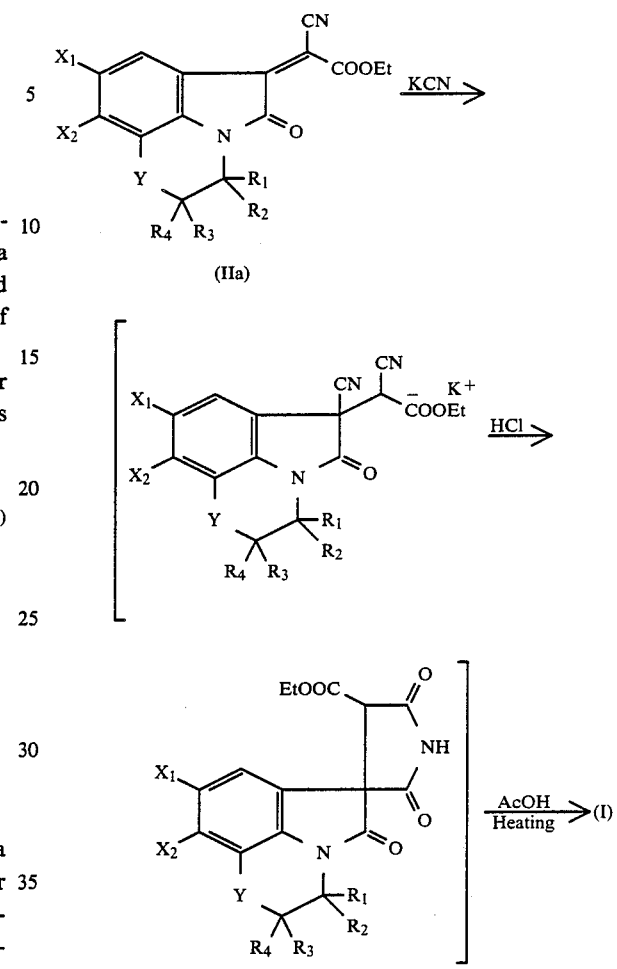

Thus the compounds of formula (I) are prepared by the addition of inorganic cyanide to the compounds of formula (IIa), wherein $X_1$, $X_2$, Y, $R_1$, $R_2$, $R_3$ and $R_4$ have the meanings defined above, and then by the decarboxylation on heat in acidic media after intramolecular cyclization in the presence of hydrogen chloride.

Defects of the former method for the mass production of the compounds of formula (I) are with perilous operation due to treating a large amount of inorganic cyanide. In addition, very expensive management is needed to prevent pollution due to disposition of a large amount of the wastes containing cyanides.

Furthermore, at the next cyclocondensation step under treatment with hydrogen chloride, gaseous hydrogen cyanide is generated from the residual inorganic cyanides so that it is difficult to maintain operators safety. If such problems had not been resolved, it is unable to perform the mass production of the compounds of formula (I).

As a result of our continuous and zealous studies for overcoming defects of the former method, we have now completed this invention through the discovering of novel processes without using inorganic cyanides for the preparation of spiro-linked pyrrolidine-2,5-diones of formula (I).

This invention relates to processes for the manufacture of spiro-linked pyrrolidine-2,5-diones, is different from the former method in respect to those described below. These points are that the compounds of formula (I) are prepared in acetic acid-sulfuric acid by intramolecular cyclocondensation of the compounds of formula (IV), which can be obtained by addition of acetonecyanohydrin to the compounds of formula (II), or by dehydration of the compounds of formula (III) prepared by adding nitromethane to the compounds of formula (II). Detailed descriptions of the invention are given below. The processes for the manufacture of the compounds of formula (I) are shown in below scheme, whereby, Ra is a lower alkyl and $X_1$, $X_2$, Y, $R_1$, $R_2$, $R_3$ and $R_4$ are same as described above.

the reaction may be proceeded at temperature in a range of 0° to 100° C., preferably at room temperature. The optimum reaction time is required for about 3 hours. Afterward, the compounds of formula (III) are dissolved in tertiary amine such as pyridine and are dehydrated by thionyl chloride or phosphorous trichloride to give the compounds of formula (IV). Excess amount of the dehydration reagents is generally used, and the reaction is advantageously proceeded at room temperature and reaction time is required for 1–5 hours. Subsequently, the compounds of formula (I) are pre-

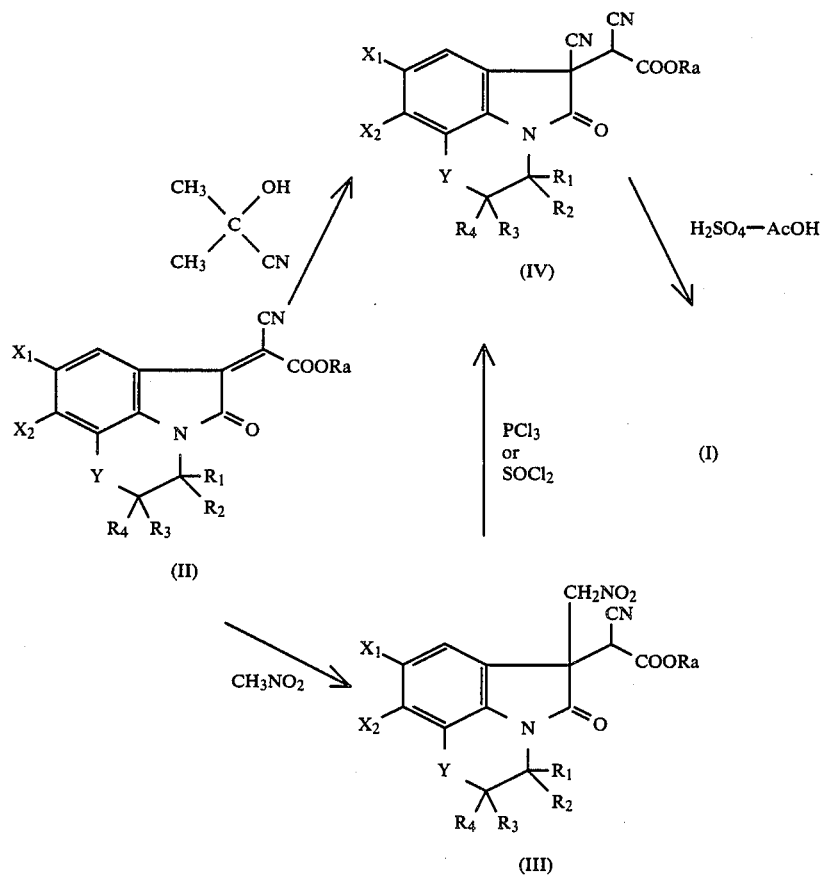

To a solution of the compounds of formula (II) in tetrahydrofuran-methyl alcohol are added acetonecyanohydrin and aqueous alkali solution. The mixture is heated under reflux. When a color of the solution changes into pale red from dark red, the reaction is approximately concluded. When acetonecyanohydrin is added in slightly excess of theoretical quantities, the reaction time may be shortened and the amounts of impurities would be decreased. That is to say, it is usually required about 3 hours for reflux, however, it is about an hour in the case of using excess acetonecyanohydrin. Sodium carbonate and potassium carbonate can be used preferably as base, and it is not necessary for using equivalent amount. The solvent used in the reaction is not limited to tetrahydrofuran-methyl alcohol.

Alternatively, the compounds of formula (III) are prepared by adding nitromethane to the suspension of the compounds of formula (II) in alkanols such as methyl alcohol, ethyl alcohol and isopropyl alcohol, in the presence of tertiary amines such as triethylamine and pyridine. Quantities of nitromethane and tertiary amine are used in slightly excess of theoretical ones, and pared by heating under reflux of the compounds of formula (IV) in the presence of sulfuric acid or polyphosphoric acid in alkanoic acids such as acetic acid. The compounds of formula (I) are obtained rapidly, in high yield and in good quality in acetic acid containing conc. sulfuric acid in proportion of 2–20%, most suitably 5%. The optimum reaction time is required for 1–2 hours.

Besides, the compounds of formula (III) and (IV) are all novel ones.

As above mentioned, the compounds of formula (I) can be obtained in sulfuric acid-acetic acid by intramolecular cyclocondensation of the compounds of formula (IV) which are obtained by adding acetonecyanohydrin to the compounds of formula (II) or by dehydration of the compounds of formula (III) prepared by adding nitromethane to compounds of formula (II). By this invented method, spiro-linked pyrrolidine-2,5-diones of formula (I), which are useful for therapeutic treatment of diabetic complications, can be advantageously obtained for industrial manufacture.

The invention will now be illustrated in the following non-limiting examples. The structure of compounds was supported with each spectral data of NMR, IR and Mass.

EXAMPLE 1

Ethyl 2-(8-chloro-6-cyano-2,3-dihydro-5-oxo-pyrrolo[1,2,3-de]-1,4-benzoxazine-6-yl)-2-cyanoacetate To a solution of ethyl 8-chloro-α-cyano-2,3-dihydro-5-oxo-$\Delta^{6,\alpha}$-pyrrolo[1,2,3-de]-1,4-benzoxazineacetate (2 g) in tetrahydrofuran (25 ml) and methanol (5 ml) were added acetonecyanohydrin (0.8 g) and 10% sodium carbonate solution, and the mixture was heated under reflux. After concentration under reduced pressure, water was added to the residue and then extracted with methylene dichloride. Evaporation of the solvent afforded dark reddish oil (2.2 g) quantitatively.

EXAMPLE 2

Ethyl 2-(8-chloro-2,3-dihydro-6-nitromethyl-5-oxopyrrolo[1,2,3-de]-1,4-benzoxazine-6-yl)-2-cyanoacetate.

To a suspension of ethyl 8-chloro-α-cyano-2,3-dihydro-5-oxo-$\Delta^{6,\alpha}$-pyrrolo[1,2,3-de]-1,4-benzoxazineacetate (9.5 g) in ethanol (100 ml) was added nitromethane (2.2 g) and triethylamine (3.6 g), and then the mixture was stirred at room temperature for 3 hours. The reaction mixture was filtered off. Filtrate was concentrated under reduced pressure, and purified to give the title compound as purple oil (8.3 g, 72.8%).

EXAMPLE 3

Ethyl 2-(8-chloro-6-cyano-2,3-dihydro-5-oxopyrrolo[1,2,3-de]-1,4-benzoxazine-6-yl)-2-cyanoacetate To a solution of ethyl 2-(8-chloro-2,3-dihydro-6-nitromethyl-5-oxopyrrolo[1,2,3-de]-1,4-benzoxazine-6-yl)-2-cyanoacetate (3 g) in pyridine (30 ml) was added phosphorous trichloride (1.6 g) on an ice bath, and stirred at room temperature for 4.5 hours. The reaction mixture was poured into water and extracted with ethyl acetate. After removal of solvent, the title compound was obtained as dark reddish oil (0.9 g, 33%) by purification.

EXAMPLE 4

8'-Chloro-2',3'-dihydrospiro[pyrrolidine-3,6'(5'H)-pyrrolo[1,2,3-de][1,4]benzoxazine]-2,5,5'-trione A solution of ethyl 2-(8-chloro-6-cyano-2,3-dihydro-5-oxopyrrolo[1,2,3-de]-1,4-benzoxazine-6-yl)-2-cyanoacetate (1 g) in sulfuric acid (0.5 ml)-acetic acid (10 ml) was heated under reflux for 2 hours. The reaction mixture was poured into ice water, and the resulting precipitate was collected by filtration. Recrystallization from acetic acid afforded colorless crystals (0.48 g, 57%), mp 271° C.

Analysis (%) for $C_{13}H_9ClN_2O_2^-$, Calcd. (Found): C, 53.34 (53.22); H, 3.09 (3.12); N, 9.57 (9.52).

This compound obtained by this method was identified with the one prepared by the former method in all respects.

What is claimed is:

1. A process for the synthesis of a spiro-linked pyrrolidine-2,5-dione of the formula:

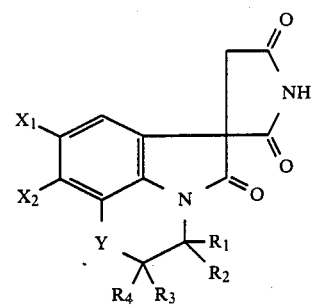

wherein $X_1$ and $X_2$ each independently represent a hydrogen atom, a halogen atom, a lower alkyl group or an alkoxy group; Y is a methylene group, an oxygen atom or a sulfur atom; $R_1$, $R_2$, $R_3$ and $R_4$ each independently represent a hydrogen atom, a lower alkyl group or the carbon atoms of which groups together form a benzene ring, comprising:

reacting acetone cyanohydrin with a compound of the formula:

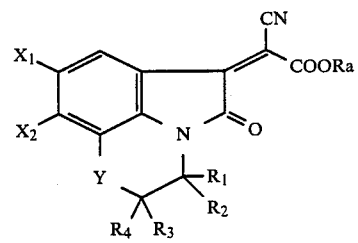

wherein Ra is a lower alkyl group and $X_1$, $X_2$, Y and $R_1$–$R_4$ each have the above-stated meanings; and heating, in the presence of an acid, the product obtained from the acetone cyanohydrin addition step of the formula:

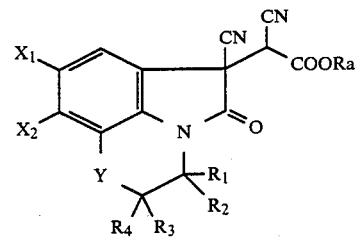

2. A process for the synthesis of a spiro-linked pyrrolidine-2,5-dione of the formula:

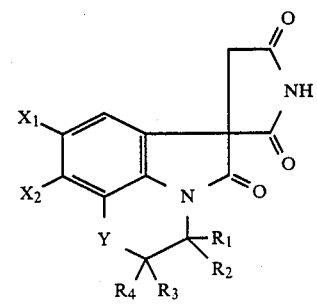

wherein $X_1$ and $X_2$ each independently represent a hydrogen atom, a halogen atom, a lower alkyl group or an alkoxy group; Y is a methylene group, an oxygen atom or a sulfur atom; $R_1$, $R_2$, $R_3$ and $R_4$ each independently represent a hydrogen atom, a lower alkyl group or the carbon atoms of which groups together form a benzene ring, comprising:

adding nitromethane to a compound of the formula:

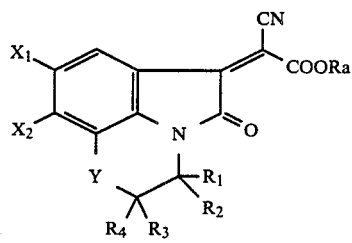

wherein Ra is a lower alkyl group and $X_1$, $X_2$, Y and $R_1$–$R_4$ each have the above-stated meanings;

dehydrating the compound obtained by nitromethane addition of the formula:

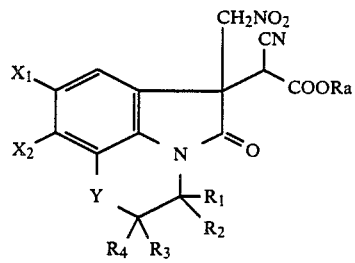

wherein Ra, $X_1$, $X_2$, Y and $R_1$–$R_4$ are each as defined above; and heating, in the presence of an acid, the dehydrated compound of the formula:

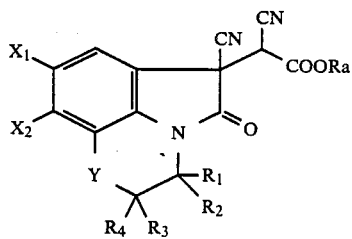

wherein Ra, $X_1$, $X_2$, Y and $R_1$–$R_4$ are each as stated above, thereby obtaining said product spiro-linked pyrrolidine-2,5-dione compound.

* * * * *